United States Patent [19]

Batzer et al.

[11] 4,060,525

[45] * Nov. 29, 1977

[54] FIVE- OR SIX-MEMBERED HETEROCYCLIC MONO -AND DIALCOHOLS

[75] Inventors: Hans Batzer, Arlesheim; Juergen Habermeier, Allschwil; Daniel Porret, Binningen, all of Switzerland

[73] Assignee: Ciba-Geigy AG, Basel, Switzerland

[*] Notice: The portion of the term of this patent subsequent to Dec. 21, 1988, has been disclaimed.

[21] Appl. No.: 568,536

[22] Filed: Apr. 16, 1975

Related U.S. Application Data

[63] Continuation of Ser. No. 262,422, June 13, 1972, abandoned, which is a continuation-in-part of Ser. No. 109,953, Jan. 26, 1971, Pat. No. 3,828,045.

[30] Foreign Application Priority Data

Jan. 30, 1970 Switzerland .......................... 1347/70
Oct. 8, 1970 Switzerland ........................ 14891/70

[51] Int. Cl.$^2$ .................. C07D 239/54; C07D 233/72
[52] U.S. Cl. ...................................... 260/260; 548/312
[58] Field of Search .............................. 260/260, 309.5

[56] References Cited

U.S. PATENT DOCUMENTS

3,828,045   8/1974   Batzer et al. ........................ 260/260

*Primary Examiner*—Paul M. Coughlan, Jr.
*Attorney, Agent, or Firm*—Vincent J. Cavalieri

[57] ABSTRACT

New mono- or dialcohols of mononuclear, five-membered or six-membered, unsubstituted or substituted N-heterocyclic compounds which contain two NH-groups in the molecule, by reaction of mononuclear, five-membered or six-membered, unsubstituted or substituted N-heterocyclic compounds, for example hydantoin, barbituric acid, uracil, dihydrouracil, parabanic acid and the corresponding derivatives, with butene oxid, 1,2-cyclopentene oxide or 1,2-cyclohexene oxide to give monoalcohols or dialcohols. These compounds are useful as intermediates for the preparation of diglycidyl compounds as set forth in German Offenlegungsschrift No. 2,104,259.

6 Claims, No Drawings

FIVE- OR SIX-MEMBERED HETEROCYCLIC MONO -AND DIALCOHOLS

This is a Continuation of now abandoned application Ser. No. 262,422 filed on June 13, 1972 which is a Continuation-in-Part of application Ser. No. 109,953, filed on Jan. 26, 1971, now U.S. Pat. No. 3,828,045.

The subject of the present invention are new mono- or dialcohols of the general formula

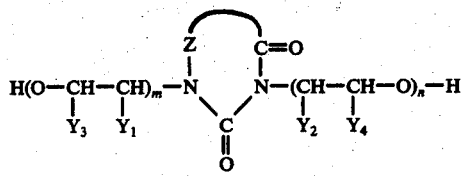

wherein $Y_1$ and $Y_2$ each denotes a hydrogen atom or a methyl group and $Y_3$ and $Y_4$ each denotes a methyl or ethyl group, the sum of the carbon atoms in the two radicals $Y_1$ and $Y_3$ or $Y_2$ and $Y_4$ having always to be 2, or wherein $Y_2$ and $Y_4$ together denote the trimethylene or tetramethylene radical, and Z denotes a nitrogen-free, divalent radical which is required to complete a five-membered or six-membered, unsubstituted or substituted, heterocyclic ring, and m and n each represent an integer having a value of 0 to 30, preferably of 0 to 4, the sum of m and n having to be at least 1.

The radical Z in the formula (I) preferably consists only of carbon and hydrogen or of carbon, hydrogen and oxygen. It can for example be a radical of formula:

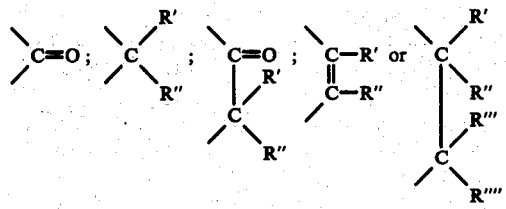

wherein R', R'', R''', R'''' independently of one another can each denote a hydrogen atom or, for example, an alkyl radical, an an alkenyl radical, a cycloalkyl radical or an optionally substituted phenyl radical.

The mono- or dialcohols of the general formula (I) can be manufactured by reacting mononuclear N-heterocyclic compounds of the general formula

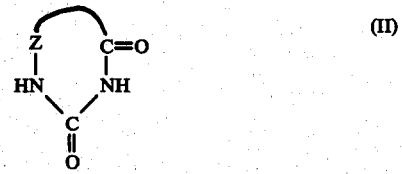

wherein Z has the same meaning as in formula (I), with butene oxide, cyclopentene oxide or cyclohexene oxide in the presence of a suitable catalyst.

The addition of the butene oxide to one or both NH groups, or the addition of the cyclopentene oxide or cyclohexene oxide to a NH group of the N-heterocyclic compounds of the formula (II) can be carried out either in the presence of acid catalysts or of alkaline catalysts with a small excess of equivalent epoxide groups of the butene oxide being employed per equivalent NH group of the N-heterocyclic compound of the formula (II).

Preferably, however, alkaline catalysts, for example tetraethylammonium chloride or tertiary amines, are used in the manufacture of monoalcohols and dialcohols of the formula (I), in which the sum of m and n is 1 or 2. However, alkali halides, for example lithium chloride or sodium chloride, can also be successfully used for this addition reaction; it also takes place without catalysts.

In the manufacture of dialcohols of the formula (I), in which the sum of m and n is greater than 2, it is preferable to start from the simple dialcohols of the formula (I), in which m and n are each 1, and further butene oxide is added to the two OH groups of this compound in the presence of acid catalysts.

The mononuclear N-heterocyclic compounds of the formula (I) used for the manufacture of the new butene oxide addition products of the formula (I) are above all hydantoin, hydantoin derivatives, barbituric acid, barbituric acid derivatives, uracil, uracil derivatives, dihydrouracil and dihydrouracil derivatives, and also parabanic acid.

Hydantoin and its preferred derivatives correspond to the general formula

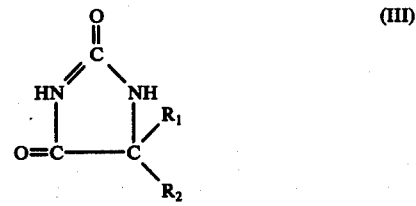

wherein $R_1$ and $R_2$ each denote a hydrogen atom or a lower alkyl radical with 1 to 4 carbon atoms, or wherein $R_1$ and $R_2$ together form a tetramethylene or pentamethylene radical. Hydantoin, 5-methylhydantoin, 5-methyl-5-ethylhydantoin, 5-n-propylhydantoin, 5-isopropylhydantoin, 1,3-diaza-spiro(4,5)-decane-2,4-dione, 1,3-diaza-spiro(4.4)-nonane-2,4-dione and preferably 5,5-dimethyl-hydantoin may be mentioned.

Barbituric acid and its preferred derivatives correspond to the general formula

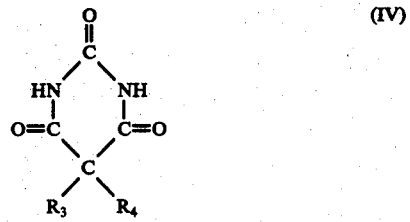

wherein $R_3$ and $R_4$ independently of one another each denote a hydrogen atom, an alkyl radical, an alkenyl radical, a cycloalkyl or cycloalkenyl radical or a substituted or unsubstituted phenyl radical.

The following may be mentioned: barbituric acid, 5-ethylbarbituric acid, 5,5-diethylbarbituric acid, 5-ethyl-5-butylbarbituric acid, 5-ethyl-5-sec-butylbarbituric acid, 5-ethyl-5-isopentylbarbituric acid, 5,5-diallyl-barbituric acid, 5-allyl-5-isopropylbarbituric acid, 5-allyl-5-sec-butylbarbituric acid, 5-ethyl-5(1'-methylbutyl)-barbituric acid, 5-allyl-5(1'methylbutyl)barbituric acid, 5-ethyl-5-phenylbarbituric acid and 5-ethyl-5(1'cyclohexen-1-yl)-barbituric acid.

Uracil and its preferred derivatives correspond to the general formula

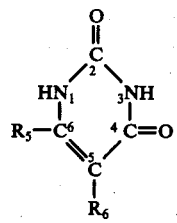
(V)

wherein $R_5$ and $R_6$ both denote hydrogen or one of the two radicals denotes a hydrogen atom and the other radical denotes a methyl group.

Uracils of the formula (V) are uracil itself, and also 6-methyl-uracil and thymin (= 5-methyl-uracil).

Dihydrouracil (= 2,4-dioxo-hexahydropyrimidine) and its preferred derivatives correspond to the general formula

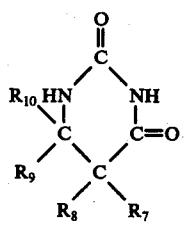
(VI)

wherein $R_7$ and $R_8$ both denote a hydrogen atom or alkyl radicals, which may be the same or different, preferably alkyl radicals with 1 to 4 carbon atoms, and $R_9$ and $R_{10}$ independently of each another each denotes a hydrogen atom or an alkyl radical.

In the above formula, the two radicals $R_7$ and $R_8$ preferably denote methyl groups, $R_9$ denotes a hydrogen atom or a lower alkyl radical with 1 to 4 carbon atoms, and $R_{10}$ denotes a hydrogen atom. The following may be mentioned: 5,6-dihydrouracil, 5,5-dimethyl-5,6-dihydrouracil (2,4-dioxo-5,5-dimethylhexahydropyrimidine) and 5,5-dimethyl-6-isopropyl-5,6-dihydrouracil (2,4-dioxo-5,5-dimethyl-6-isopropylhexahydropyrimidine).

EXAMPLE 1

3-(2'-Hydroxy-n-butyl)-5,5-dimethylhydantoin 256.3 g of 5,5-dimethylhydantoin (2 mols) and 2.54 g of lithium chloride in 300 ml of dimethylformamide are together stirred at 65° C. 158.8 g of 1,2-butene oxide (2.2 mols) are slowly added dropwise over the course of 2 hours at this temperature. Thereafter the mixture is stirred for a further 4 hours at 100° C. The solution is cooled to room temperature and filtered, and the filtrate is then concentrated on a rotary evaporator at 70° C/20 mm Hg and dried to constant weight at 90° C/0.1 mm Hg. A crystalline, light yellow crude product is obtained in quantitative yield (400.1 g). The substance can be purified by recrystallisation from acetone. Colourless, glistening crystals melting at 87°-88.5° C are obtained.

Elementary analysis shows:

| found: | calculated: |
|---|---|
| 53.7 % C | 53.98 % C |
| 8.3 % C | 8.06 % H |
| 13.94 % N | 13.99 % N |

The mass spectrum shows a molecular weight of 200 (theory 200.22). The following characteristic fragments are found, inter alia (in mass numbers): 183, 171, 142, 114, 113 and 99.

The substance thus corresponds to the following structure:

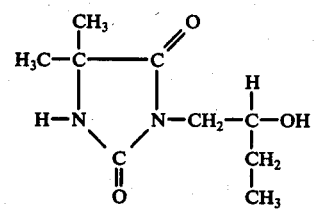

EXAMPLE 2

1,3-Di-(2'-hydroxy-n-butyl)-5,5-dimethylhydantoin 256.3 g of 5,5-dimethylhydantoin (2 mols), 4.25 g of lithium chloride and 300 ml of dimethylformamide are stirred at 65° C. 396.2 g of 1,2-butene oxide (5.5 mols) are added dropwise thereto over the course of 2 hours. The temperature of the batch is raised from 65° to 95° C over the course of 2 hours and the mixture is stirred for a further 3 hours at this temperature. Thereafter it is cooled to room temperature and filtered. The filtrate is concentrated at 70° C on a rotary evaporator under 15 mm Hg and is dried to constant weight at 90° C and 10.1 mm Hg. 534 g of a clear, light brown liquid adduct (98% of theory) are obtained. Both the IR spectrum and the H—NMR spectrum show, through the absence of the signals for N—H and the presence of —OH frequencies, that the desired substance has been produced. Elementary analysis shows:

| found: | calculated: |
|---|---|
| 10.49 % N | 10.29 % N |
| 8.85 % H | 8.89 % H |

The new compound thus has the following structure:

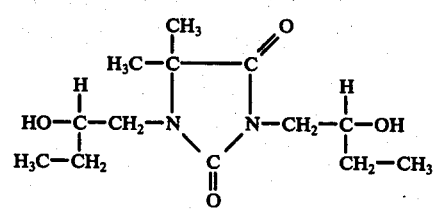

EXAMPLE 3

3-(2'-Hydroxycyclohexyl)-5,5-dimethylhydantoin

A mixture of 128.1 g of 5,5-dimethylhydantoin (1 mol), 1 g of lithium chloride and 200 ml of dimethylformamide is stirred at 100° C in a 500 ml glass apparatus having a stirrer, thermometer, dropping funnel and reflux condenser. 100 g of cyclohexene oxide (1.02 mols) are added dropwise to this solution over the course of 120 minutes, whilst stirring. Thereafter the mixture is stirred for a further 5 hours at 125°–130° C. After cooling to about 60° C, the reaction mixture is filtered and is concentrated to dryness on a rotary evaporator at 70° C under a waterpump vacuum. Thereafter the residue is dried to constant weight at 90° C/0.1 Hg. 217.8 g of a yellowish, crystalline material (96.4% of theory) are obtained, and this can be recrystallised, for example from acetone. The purified product melts at 159°–161° C. Elementary analysis shows the following values:

found: 58.6%,C; 12.4%,N. calculated: 58.4%,C; 12.4%,N.

The proton-magnetic resonance spectrum (60 Mc-HNMR, in $CDCl_3$, using tetramethylsilane as an internal standard) shows, inter alia, through the presence of the signals of $N_1$—H ($\delta = 7.4$), the OH signals and the $CH_2$ signals and the hydantoin-$CH_3$ signals, that the desired monoadduct has been produced:

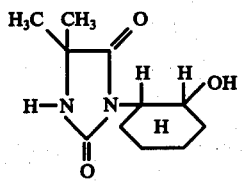

EXAMPLE 4

368.4 g of 5,5-dimethyl-6-isopropyl-5,6-dihydrouracil (= 2,4-dioxo-5,5-dimethyl-6-isopropylhexahydropyrimidine) (2 mols) in 2000 ml of dimethylformamide are stirred with 12 g of lithium chloride at 60°–65° C in accordance with Example 2). 432.6 g of 1,2-butene oxide (6.0 mols) are added dropwise thereto over the course of 120 minutes, with slight stirring. The temperature is raised to 95° C over the course of one hour and the mixture is stirred for a further 12 hours at this temperature. Working-up is carried out precisely according to Example 2).

A light yellow, clear, highly viscous substance is obtained in 88% yield (578 g).

The proton-magnetic resonance spectrum (60 Mc H-NMR, recorded in $CDCl_3$ at 35° C, using tetramethylsilane as an internal standard) shows, through the presence of the following signals, that the product has the structure given below:

$\delta = 0.7 - 1.4$: multiplet: 20 protons $2 \times$ H—C— $2 \times H_3C—CH_2$ $\delta = 1.6 - 2.3$: multiplet: 4 protons $2 \times$ C—$CH_2$—C $\delta = 2.9 - 3.15$: multiplet: 2 protons $2 \times$ H—C<

$\delta = 3.3 - 4.2$: multiplet: remaining protons

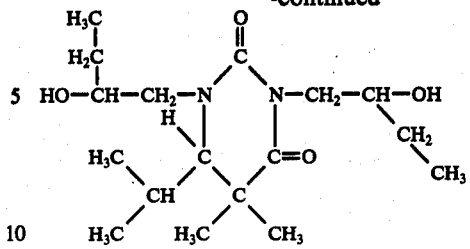

We claim:
1. A mono- or dialcohol of the formula

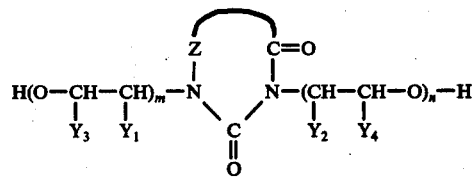

wherein $Y_1$ and $Y_2$ each denotes hydrogen or methyl and $Y_3$ and $Y_4$ each denotes methyl or ethyl, the sum of the carbon atoms in $Y_1$ and $Y_3$ or $Y_2$ and $Y_4$ having always to be 2, or wherein $Y_2$ and $Y_4$ together denote trimethylene or tetramethylene, and Z represents a member selected from the group consisting of a divalent residue of the formulae

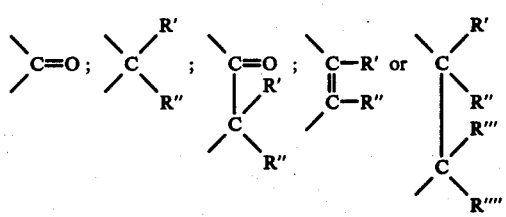

wherein R', R'', R''' and R'''' each represents a member selected from the group consisting of alkyl with 1 to 4 carbon atoms, alkenyl with 2 to 4 carbon atoms, cyclohexyl, cyclohexenyl, and phenyl, or when Z represents the formula

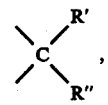

R' and R'' together denote tetramethylene and pentamethylene, and m and n each represents an integer having a value of 0 to 30 with the sum of m and n having to be at least 1.

2. A compound as claimed in claim 1 wherein in the formula (I) m and n each represents an integer having a value of 0 to 4 with the seem of m and n having to be at least 1.

3. A compound as claimed in claim 1 which is 3-(2-hydroxy-n-butyl)-5,5-dimethylhydantoin.

4. A compound as claimed in claim 1 which is 1,3-di-(2'-hydroxy-n-butyl)-5,5-dimethylhydantoin.

5. A compound as claimed in claim 1 which is 3-(2'-hydroxycyclohexyl)-5,5-dimethylhydantoin.

6. A compound as claimed in claim 1 which is 1,3-di-(2'-hydroxy-n-butyl)-5,5-dimethyl-6-isopropyl-5,6-dihydrouracil.

* * * * *